(12) United States Patent
Kano et al.

(10) Patent No.: US 9,612,230 B2
(45) Date of Patent: Apr. 4, 2017

(54) WATER QUALITY MEASURING DEVICE

(71) Applicant: Miura Co., Ltd., Matsuyama-shi, Ehime-ken (JP)

(72) Inventors: Katsuaki Kano, Matsuyama (JP); Yusuke Hamada, Matsuyama (JP); Yasuyuki Arimitsu, Matsuyama (JP)

(73) Assignee: MIURA Co., Ltd., Matsuyama-shi, Ehime-ken (JP)

( * ) Notice: Subject to any disclaimer, the term of this patent is extended or adjusted under 35 U.S.C. 154(b) by 0 days.

(21) Appl. No.: 14/833,931

(22) Filed: Aug. 24, 2015

(65) Prior Publication Data
US 2015/0362471 A1 Dec. 17, 2015

Related U.S. Application Data

(63) Continuation-in-part of application No. 13/206,840, filed on Aug. 10, 2011, now abandoned.

(30) Foreign Application Priority Data

Jun. 21, 2011 (JP) .................................. 2011-136938

(51) Int. Cl.
*G01N 33/18* (2006.01)
*A61J 1/14* (2006.01)
(Continued)

(52) U.S. Cl.
CPC ............ *G01N 33/18* (2013.01); *A61J 1/1475* (2013.01); *B32B 7/12* (2013.01); *B32B 15/08* (2013.01);
(Continued)

(58) Field of Classification Search
CPC .. C02F 2103/42; C02F 1/685; C02F 2209/22; G01N 33/1886; G01N 27/4167;
(Continued)

(56) References Cited

U.S. PATENT DOCUMENTS 2,019,221 A * 10/1935 Hastings .................. G01K 5/62
374/156
3,162,813 A * 12/1964 Piccinini ................ H04B 1/034
174/550
(Continued)

FOREIGN PATENT DOCUMENTS

| CN | 1526373 A | 9/2004 |
|---|---|---|
| CN | 101316702 A | 12/2008 |

(Continued)

*Primary Examiner* — David A Rogers
(74) *Attorney, Agent, or Firm* — Fox Rothschild LLP (57) ABSTRACT

A water quality measuring device comprises a measurement cell (10), a sample water supply unit (80), a reagent supply unit (30), an agitating unit (17), a measuring unit (20) and a control unit (90). The sample water supply unit (80) includes an inlet channel (12) configured to supply the measurement cell (10) with sample water and an outlet channel (13) configured to discharge sample water from the measurement cell (10). The inlet channel (12) is connected to a flow channel (2) configured to supply sample water, and includes a filter (13) and an electromagnetic valve (15). The control unit (90) opens the electromagnetic valve (15) for supplying sample water to allow sample water, from which foreign substances are removed by the filter (13), to flow into the measurement cell (10).

8 Claims, 5 Drawing Sheets

(51) Int. Cl.
  *B32B 7/12* (2006.01)
  *B32B 15/08* (2006.01)
  *B32B 15/20* (2006.01)
  *B32B 27/08* (2006.01)
  *B32B 27/36* (2006.01)
  *G01N 21/78* (2006.01)
  *A61J 1/10* (2006.01)
  *G01N 1/20* (2006.01)

(52) U.S. Cl.
  CPC ............. *B32B 15/20* (2013.01); *B32B 27/08* (2013.01); *B32B 27/36* (2013.01); *G01N 21/78* (2013.01); *G01N 33/1893* (2013.01); *A61J 1/10* (2013.01); *B32B 2255/10* (2013.01); *B32B 2255/205* (2013.01); *B32B 2307/51* (2013.01); *B32B 2439/80* (2013.01); *G01N 2001/2071* (2013.01)

(58) Field of Classification Search
  CPC . G01N 27/4168; G01N 21/59; G01N 33/1893
  See application file for complete search history.

(56) References Cited

U.S. PATENT DOCUMENTS

| | | | |
|---|---|---|---|
| 3,331,039 A | 7/1967 | McGary | |
| 3,331,421 A | 7/1967 | Lambert | |
| 3,466,450 A * | 9/1969 | Goodman | G01N 21/78 250/357.1 |
| 3,504,145 A * | 3/1970 | Layher | G08B 21/084 200/61.2 |
| 3,576,998 A | 5/1971 | Deutsch et al. | |
| 3,799,193 A | 3/1974 | Greenwood et al. | |
| 4,015,626 A * | 4/1977 | Thordarson | G05D 7/0106 137/375 |
| 4,023,607 A | 5/1977 | Jensen et al. | |
| 4,030,361 A * | 6/1977 | Fortune | G01K 13/00 374/156 |
| 4,049,033 A | 9/1977 | Ralston, Jr. | |
| 4,056,470 A * | 11/1977 | Carpenter | B01F 1/0038 210/167.11 |
| 4,069,405 A * | 1/1978 | Fima | G01F 23/70 200/84 C |
| 4,096,897 A | 6/1978 | Cammarata, III | |
| 4,270,533 A | 6/1981 | Andreas | |
| 4,335,770 A | 6/1982 | Kulle et al. | |
| 4,435,095 A * | 3/1984 | Jones | G01K 1/065 116/216 |
| 4,503,563 A * | 3/1985 | Johnson | F21S 9/02 362/158 |
| 4,510,487 A * | 4/1985 | Wolfe | G08B 21/084 200/84 C |
| 4,534,758 A | 8/1985 | Akers et al. | |
| 4,550,011 A * | 10/1985 | McCollum | G01N 33/1893 204/409 |
| RE32,065 E | 1/1986 | Ralston, Jr. et al. | |
| 4,573,967 A | 3/1986 | Hargrove et al. | |
| 4,607,764 A | 8/1986 | Christine | |
| 4,769,137 A * | 9/1988 | Powell, Jr. | E04H 4/1281 210/139 |
| 4,781,810 A * | 11/1988 | Tucker | C02F 1/4674 204/228.2 |
| 4,823,625 A * | 4/1989 | Hamilton | G07C 3/00 324/700 |
| 4,900,432 A * | 2/1990 | Arnold | E04H 4/1263 15/1.7 |
| 4,917,782 A * | 4/1990 | Davies | B01D 17/06 204/228.3 |
| 4,940,946 A * | 7/1990 | Nazaryan | G01N 33/1886 324/149 |
| 5,036,615 A * | 8/1991 | Lu | A01K 93/02 43/17 |
| 5,105,992 A * | 4/1992 | Fender | A47K 5/1217 222/181.2 |
| 5,115,222 A * | 5/1992 | Peralta | G08B 21/084 340/566 |
| 5,124,960 A * | 6/1992 | Miller | G04B 37/086 368/107 |
| 5,152,610 A * | 10/1992 | Hallett | E04H 4/14 374/141 |
| 5,169,236 A * | 12/1992 | Iest | G01K 1/045 374/142 |
| 5,189,350 A * | 2/1993 | Mallett | G01D 1/14 318/434 |
| 5,218,304 A * | 6/1993 | Kinlen | G01N 27/4166 204/412 |
| 5,334,180 A | 8/1994 | Adolf et al. | |
| 5,351,432 A * | 10/1994 | Tse | A01K 93/02 43/17 |
| 5,369,796 A * | 11/1994 | Kung | H04B 1/08 441/12 |
| 5,460,556 A * | 10/1995 | Logan | B63B 22/18 441/2 |
| 5,514,123 A | 5/1996 | Adolf et al. | |
| 5,518,635 A * | 5/1996 | Kohlman | E04H 4/1281 210/167.11 |
| 5,556,259 A | 9/1996 | Hlavenka | |
| 5,621,390 A * | 4/1997 | Neal | G08B 21/182 340/584 |
| 5,654,692 A * | 8/1997 | Baxter, Jr. | B63B 22/16 340/539.13 |
| 5,681,110 A * | 10/1997 | Burzacchi | G01K 1/06 374/142 |
| 5,752,282 A * | 5/1998 | Silveri | C02F 1/46104 4/541.1 |
| 5,759,384 A * | 6/1998 | Silveri | C02F 1/008 204/212 |
| 5,821,405 A * | 10/1998 | Dickey | G01D 11/24 73/170.29 |
| 5,938,414 A | 8/1999 | Kayahara et al. | |
| 5,944,709 A | 8/1999 | Barney et al. | |
| 5,996,138 A * | 12/1999 | Kentch | E04H 4/1209 210/167.12 |
| 6,007,693 A * | 12/1999 | Silveri | C02F 1/008 205/335 |
| 6,071,626 A | 6/2000 | Frisk | |
| 6,113,858 A * | 9/2000 | Tang | G01N 21/78 422/66 |
| 6,149,579 A | 11/2000 | Lee | |
| 6,198,106 B1 | 3/2001 | Barney et al. | |
| 6,199,729 B1 | 3/2001 | Drzymkowski | |
| 6,203,170 B1 * | 3/2001 | Patrick | A01K 79/02 362/158 |
| 6,223,359 B1 * | 5/2001 | Oltmanns | E04H 4/12 137/392 |
| 6,225,900 B1 * | 5/2001 | Keon | G08B 1/08 340/384.1 |
| 6,228,272 B1 * | 5/2001 | Gola | C02F 1/008 137/268 |
| 6,238,553 B1 * | 5/2001 | Lin | C02F 1/008 204/412 |
| 6,276,200 B1 * | 8/2001 | Cazden | E04H 4/12 137/428 |
| 6,294,086 B1 * | 9/2001 | Reeves | B01F 1/0027 210/198.1 |
| 6,309,538 B1 * | 10/2001 | Khan | C02F 1/008 210/143 |
| 6,315,424 B1 * | 11/2001 | Hui | F21S 8/00 362/101 |
| 6,340,431 B2 * | 1/2002 | Khan | 210/138 |
| 6,476,721 B1 * | 11/2002 | Diebold | G08B 21/088 340/566 |
| 6,653,842 B2 * | 11/2003 | Mosley | G01N 27/4168 204/400 |
| 6,792,956 B2 * | 9/2004 | Bredo | E04H 4/1654 134/10 |
| 6,855,300 B2 * | 2/2005 | Cormier | A61L 2/18 422/261 |

(56) References Cited

U.S. PATENT DOCUMENTS

| | | | |
|---|---|---|---|
| 7,037,038 B1* | 5/2006 | Haski | B63B 35/32 210/242.1 |
| 7,245,853 B2 | 7/2007 | Muramatsu et al. | |
| 7,926,925 B2 | 4/2011 | Ikezaki | |
| 9,052,302 B2* | 6/2015 | Lundgreen | G01N 21/3151 |
| 2001/0036326 A1 | 11/2001 | Ichikawa | |
| 2001/0045380 A1* | 11/2001 | Khan | C02F 1/008 210/85 |
| 2002/0179728 A1* | 12/2002 | Beidokhti | B05B 17/08 239/20 |
| 2003/0092020 A1* | 5/2003 | Carson | C02F 3/006 435/6.19 |
| 2003/0150877 A1 | 8/2003 | Sturm et al. | |
| 2003/0227394 A1* | 12/2003 | Rothgeb | A47L 15/4297 340/870.01 |
| 2004/0031329 A1* | 2/2004 | Carpenter | G01F 23/26 73/861.19 |
| 2004/0035465 A1* | 2/2004 | Cazden | E04H 4/12 137/392 |
| 2004/0066313 A1* | 4/2004 | Ong | G08C 19/04 340/870.11 |
| 2004/0098211 A1* | 5/2004 | Binz | G01N 1/14 702/50 |
| 2004/0104130 A1* | 6/2004 | Mosley | G01N 27/4168 205/787.5 |
| 2004/0208499 A1* | 10/2004 | Grober | B63B 22/24 396/428 |
| 2005/0061752 A1* | 3/2005 | Tarara | A01M 7/0092 210/739 |
| 2005/0220169 A1* | 10/2005 | McGowan-Scanlon | G01N 33/1886 374/156 |
| 2005/0225766 A1* | 10/2005 | Hansen | G01N 15/1459 356/436 |
| 2005/0279677 A1* | 12/2005 | Lin | C02F 1/688 210/96.1 |
| 2006/0054568 A1* | 3/2006 | Jones | C02F 1/36 210/748.03 |
| 2006/0092630 A1* | 5/2006 | Kennedy | F21S 8/00 362/157 |
| 2006/0283808 A1* | 12/2006 | Kadlec | C02F 1/76 210/746 |
| 2007/0034249 A1* | 2/2007 | Romano | F21S 8/00 136/244 |
| 2010/0247936 A1 | 9/2010 | Chang et al. | |
| 2011/0212538 A1* | 9/2011 | Lundgreen | G01N 21/3151 436/164 |
| 2012/0328219 A1* | 12/2012 | Kano | A61J 1/1475 383/36 |
| 2015/0233817 A1* | 8/2015 | Lundgreen | G01N 21/31 422/82.06 |

FOREIGN PATENT DOCUMENTS

| | | | | |
|---|---|---|---|---|
| CN | 101568486 A | | 10/2009 | |
| DE | 19951436 A1 | * | 5/2000 | ........... E04H 4/1263 |
| JP | H10-325801 A | | 12/1998 | |
| JP | 3186577 B2 | | 7/2001 | |
| JP | 3214400 B2 | | 10/2001 | |
| JP | 2002-193275 A | | 7/2002 | |
| JP | 2002-255199 A | | 9/2002 | |
| JP | 2004-196414 A | | 7/2004 | |
| JP | 2006-182436 A | | 7/2006 | |
| JP | 2008-074459 A | | 4/2008 | |
| WO | 2007/038488 A2 | | 4/2007 | |
| WO | 2008/078075 A2 | | 7/2008 | |

* cited by examiner

WATER QUALITY MEASURING DEVICE

INCORPORATION BY REFERENCE

This application is a divisional application of U.S. patent application Ser. No. 13/206,840 filed on Aug. 10, 2011 which claims priority under 35 U.S.C. §119 to Japanese Patent Application No. 2011-136938 filed on Jun. 21, 2011, the content of which is incorporated herein by reference in its entirety.

BACKGROUND OF THE INVENTION

1. Field of the Invention

The present invention relates to a water quality measuring device having a reagent supply unit.

2. Description of Related Art

There is known a measuring device that measures dissolved oxygen concentration, hardness, pH, residual chlorine concentration, and the like of supply water to boilers and service water and drainage water to cooling towers and various other water treatment plants by adding a predetermined medicine to sample water obtained in a cell, and detecting a change of the sample water caused by the addition of the medicine as a change in intensity of transmitted light.

With this type of measuring devices, an improvement of medicine adding devices have been made for use in automatic measurement. For example, such a device and a mechanism are conventionally known as an adding device including a medicine cartridge, and an adding mechanism for gradually adding a medicine from the medicine cartridge to sample water in a cell. In those device and mechanism, the medicine cartridge is provided with a medicine package housed within a case, and the medicine package includes a container for containing a fluid medicine, a tube body (connecting unit) for connecting an exterior and an interior of the container, and a tube made of an elastic material connected to the tube body on one end and having a nozzle for discharging the medicine on the other end. The adding mechanism is configured to pull out the tube by rotating a pressing roller to cause the medicine to flow from the container into the tube through the tube body, and to discharge the medicine through the nozzle.

The container used for the medicine package is a molded product made of a resin material such as a polypropylene resin or a polyethylene resin, and maintains a certain shape. Therefore, in order to stably discharge the medicine through the nozzle of the tube by the adding mechanism, it is necessary to provide the container with an inlet for external air. However, external air flowing into the container through the inlet may possibly denature the medicine within the container. For example, in the measurement of dissolved oxygen concentration and residual chlorine concentration of the sample water, it is necessary to add a redox coloring reagent as a medicine to the sample water. However, when this type of coloring reagent is exposed to external air, the reagent itself is oxidized-reduced. Therefore, an application of redox medicines to the adding device described above is practically difficult.

SUMMARY OF THE INVENTION

The present invention provides a water quality measuring device, for example, measuring a water quality index of sample water.

A water quality measuring device according to the present invention comprising: a measurement cell configured to pool sample water; a sample water supply unit configured to supply the measurement cell with sample water; a reagent supply unit configured to supply the measurement cell with a reagnet to react with a water quality index substance; an agitating unit provided at a bottom of the measurement cell; a measuring unit configured to measure intensity of transmitted light of light having a required wavelength through sample water; and a control unit configured to control operations of the sample water supply unit, the reagent supply unit, the agitating unit, and the measuring unit. The sample water supply unit includes an inlet channel configured to supply the measurement cell with sample water and an outlet channel configured to discharge sample water from the measurement cell. The inlet channel is connected to a flow channel configured to supply sample water, and includes a filter and an electromagnetic valve. The control unit opens the electromagnetic valve for supplying sample water to allow sample water, from which foreign substances are removed by the filter, to flow into the measurement cell.

In one aspect of the water quality measuring device, the inlet channel further includes a constant flow valve. The control unit opens the electromagnetic valve for supplying sample water to allow sample water, from which foreign substances are removed by the filter and of which flow rate is controlled by the constant flow valve, to flow into the measurement cell.

In one aspect of the water quality measuring device, the measurement cell has a pair of light transmission windows facing each other and provided in side walls. The measuring unit includes a light-emitting diode and a phototransistor facing each other with the light transmission windows sandwiched therebetween, and in a state where the measurement cell pools sample water from which foreign substances are removed by the filter. The control unit operates the measuring unit to measure intensity of transmitted light through the sample water.

In one aspect of the water quality measuring device, the agitating unit includes an agitator rotatably provided on the bottom of the measurement cell and a stator provided outside the measurement cell. The control unit energizes an electromagnetic induction coil of the stator to rotate the agitator while sample water is supplied and the reagent is injected.

In one aspect of the water quality measuring device, the reagent supply unit includes a reagent cartridge removably provided at an opening of the measurement cell. The reagent cartridge includes a cartridge case and a medicine package housed in the cartridge case. The medicine package includes a container configured to contain the reagent, a tube body provided at a lower edge of the container and configured to connect an interior and an exterior of the container, a first tube having a first end coupled to the tube body and made of an elastic material, and a nozzle connected to a second end of the first tube and configured to discharge the reagent. The nozzle includes a nozzle main body having a closed tip end and a second tube made of an elastic material. The nozzle main body has a discharge hole penetrating a side surface close to the tip end and a barb provided on an outer circumferential surface close to the tip end. The second tube is attached to the tip end of the nozzle main body and covers the barb, to be retained to the nozzle main body and close the discharge hole.

In one aspect of the water quality measuring device, the elastic material for the first tube is binary fluorine rubber or polyolefin elastomer. The elastic material for the second tube is polyolefin elastomer.

In one aspect of the water quality measuring device, the nozzle main body includes a stepped section provided substantially in a center of an outer circumference in a length direction, a groove provided around an outer circumference of the stepped section close to a tip end, and a seal ring attached to the groove. When the reagent cartridge is attached, the nozzle is disposed such that a tip end of the nozzle protrudes into the measurement cell and airtightly attached to an inner circumferential surface of the measurement cell by the seal ring.

In one aspect of the water quality measuring device, the cartridge case includes a container housing and a tubular portion extended from a bottom surface of the container housing. The tubular portion includes a slit provided vertically, a curved surface recessed arcuately and provided substantially in a vertical center of a surface facing the slit, a tube body stopping piece provided at a base end, and a nozzle stopping piece provided at a tip end. The tube body includes a first receiving section provided at a portion protruding from the container. The nozzle main body includes a second receiving section provided at a base end. The container is disposed in the container housing with the first receiving section being engaged with the tube body stopping piece. The first tube is disposed in the tubular portion with the second receiving section being engaged with the nozzle stopping piece.

In one aspect of the water quality measuring device, the reagent supply unit further includes a discharge mechanism configured to discharge the reagent from the reagent cartridge to the measurement cell. The discharge mechanism includes a rotary driving shaft provided outside the slit and connected to a motor, a driving arm having a first end coupled to the rotary driving shaft, and a pressing roller rotatably attached to a second end of the driving arm, the reagent is discharged into sample water from the discharge hole through a gap provided between the nozzle main body and the second tube when the pressing roller entering and exiting the slit presses the first tube toward the curved surface. The control unit drives the motor of the discharge mechanism for injecting the reagent, to intermittently inject a certain amount of the reagent into sample water every time the driving arm rotates.

In one aspect of the water quality measuring device, the container is entirely configured by soft sheets and provided as a bag having a gusset on either side, the interior of the container through lamination of interior surfaces of the soft sheets formed in a funnel shape with the tube body as a stem.

In one aspect of the water quality measuring device, each of the soft sheets is configured as a laminated sheet including a linear low density polyethylene resin film layer, a stretch polyamide resin film layer, an aluminum foil layer, and a stretch polyethylene terephthalate resin film layer, laminated from inside to outside of the container.

In one aspect of the water quality measuring device, each of the soft sheets is configured as a laminated sheet including a linear low density polyethylene resin film layer, an aluminum oxide vapor deposition polyamide resin film layer, and a stretch polyethylene terephthalate resin film layer, laminated from inside to outside of the container.

DETAILED DESCRIPTION OF THE INVENTION

Figure 1:
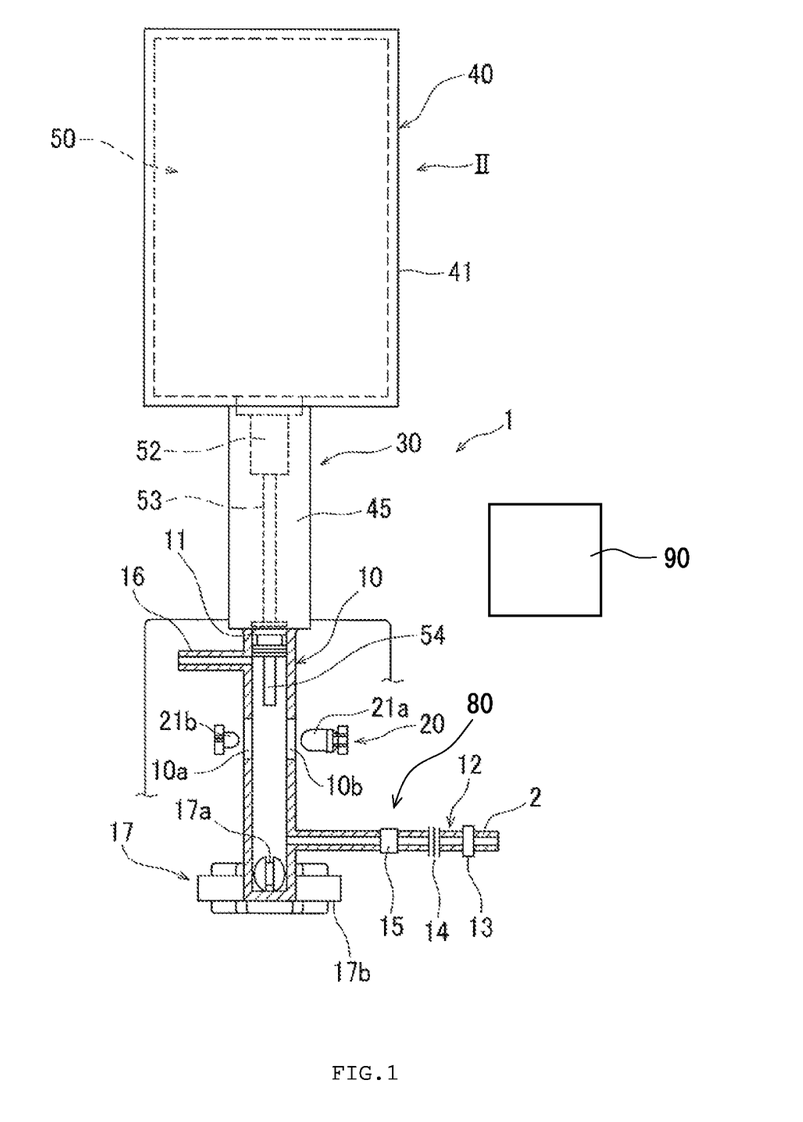
FIG. 1 is a schematic view illustrating a water quality measuring device having a medicine package according to one embodiment of the present invention.
Figure 2:
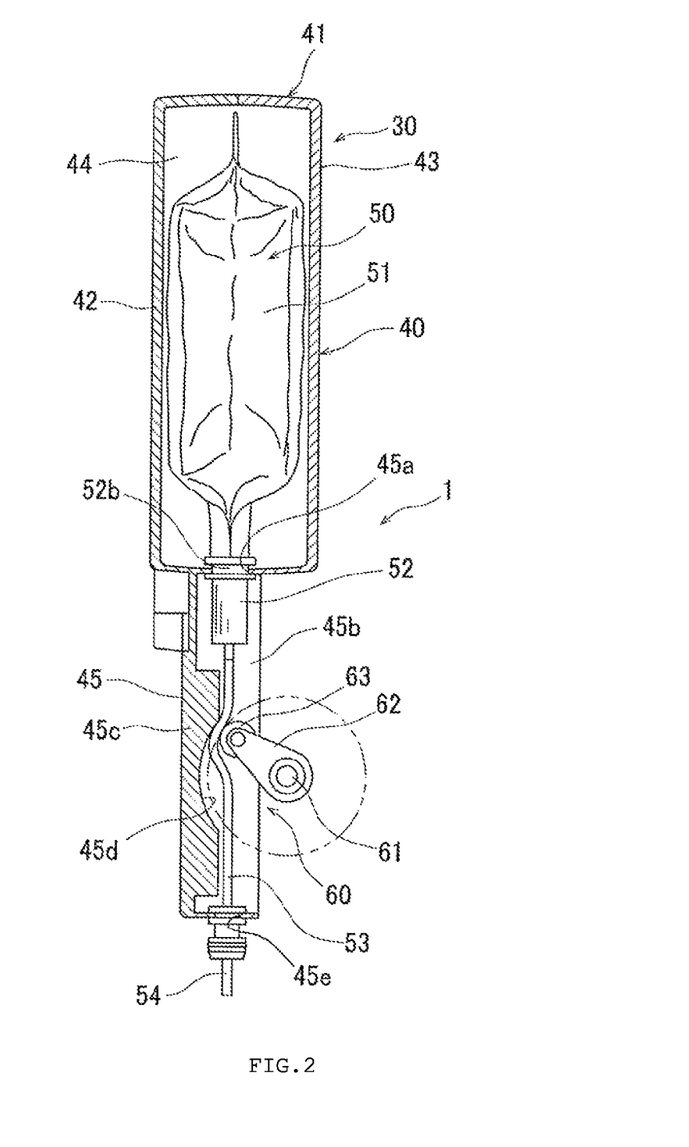
FIG. 2 is a vertical cross-sectional view illustrating a reagent supply unit provided for the water quality measuring device, seen from a direction of II in FIG. 1.

A water quality measuring device having a medicine package according to one embodiment of the present invention will be described with reference to FIG. 1 and FIG. 2. Referring to FIG. 1 and FIG. 2, a water quality measuring device 1 is configured to measure dissolved oxygen concentration in sample water, and provided with a measurement cell 10, a measuring unit 20, a reagent supply unit 30 and a sample water supply unit 80 as major components.

The measurement cell 10 is, for example, an opaque container made of a PPS (polyphenylene sulfide) resin molded into a tubular shape, and having a pair of light transmission windows 10a and 10b facing toward each other set in respective side walls and an opening 11 at the top. Further, an inlet channel 12 connected to a flow channel 2 and configured to supply the water quality measuring device 1 with sample water to be measured is provided at a portion of the side wall of the measurement cell 10 near a bottom. The inlet channel 12 includes a filter 13, a constant flow valve 14, and an electromagnetic valve 15 in this order from the side of the flow channel 2, and the valves are set in a manner that allows supply of sample water from the flow channel 2 to the measurement cell 10. In addition, an outlet channel 16 configured to discharge the sample water outside is provided at a portion of the side wall of the measurement cell 10 near the opening 11. The inlet channel 12, the filter 13, the constant flow valve 14, the electromagnetic valve 15 and the outlet channel 16 configure the sample water supply unit 80.

Moreover, an agitating unit 17 is provided at a portion of the bottom of the measurement cell 10. The agitating unit 17 includes an agitator 17a and a stator 17b. The agitator 17a is rotatably provided on the bottom of the measurement cell 10, and contains a magnet (not illustrated). The stator 17b is provided outside the measurement cell 10 so as to surround the agitator 17a, and includes an electromagnetic induction coil. The electromagnetic induction coil is configured to be supplied with current from a power source (not illustrated).

The measuring unit 20 is configured to measure intensity of transmitted light of light having a required wavelength through the sample water, and includes a light emitter 21a and a light receiver 21b that are facing toward each other with the light transmission windows 10a and 10b sandwiched therebetween. Here, the light emitter 21a is, for example, an LED (light-emitting diode) capable of emitting light of a required wavelength, and the light receiver 21b is, for example, a phototransistor capable of receiving the light from the light emitter 21a that passes through the light transmission windows 10a and 10b.

The reagent supply unit 30 is, as shown in FIG. 2, provided with a reagent cartridge 40 disposed in a manner removable from the opening 11 of the measurement cell 10, and a discharge mechanism 60 configured to discharge a reagent from the reagent cartridge 40 to the measurement cell 10 as major components. The reagent cartridge 40 includes a hollow cartridge case 41 and a medicine package 50 housed in the case.

The cartridge case 41 is a resin molded product and is divided into two pieces of a front case 42 and a back case 43 in order to house the medicine package 50 therein. The cartridge case 41 formed by combining the front case 42 and the back case 43 includes a container housing 44 that is formed basically in a cuboid shape and a tubular roller in-out unit 45 (i.e. a tubular portion) that extends from a center of a bottom surface of the container housing 44. A tube body stopping piece 45a is provided at a base end of the roller in-out unit 45 toward an interior of the cartridge case 41. The tube body stopping piece 45a is a projection for holding a tube body 52 (to be described later) of the medicine package 50. Further, a nozzle stopping piece 45e is provided at a tip end of the roller in-out unit 45 toward the interior of the cartridge case 41. The nozzle stopping piece 45e is a projection for holding a nozzle 54 (to be described later) of the medicine package 50. Moreover, a slit 45b that extends in a vertical direction is provided on a side of the back case 43 of the roller in-out unit 45. Furthermore, a pressing surface 45c facing toward the slit 45b is provided in the vertical direction for an inner surface of the roller in-out unit 45 on a side of the front case 42. The pressing surface 45c includes a curved surface 45d that is recessed in an arc in a substantial central portion in the vertical direction.

Figure 3:
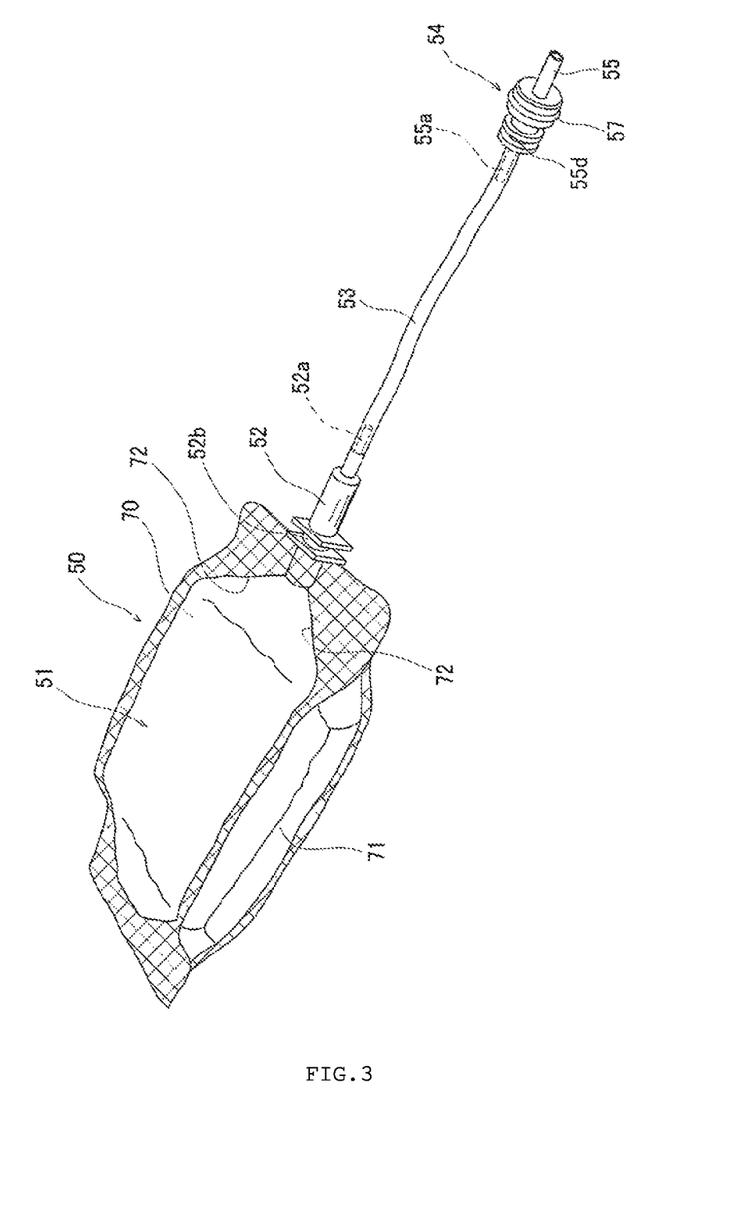
FIG. 3 is a perspective view illustrating the medicine package.

As shown in FIG. 3, the medicine package 50 includes a container 51 configured to contain a fluid reagent (medicine), the tube body 52, a tube 53 (i.e. a first tube), and the nozzle 54. The container 51 is, for example, a bag configured by bonding periphery portions (shaded areas in FIG. 3) of several pieces of soft sheets 70 cut in a desired shape in an air tight manner, and includes a gusset 71 on each side end that expands in a through-thickness direction when a reagent is filled therein.

It should be noted that the reagent contained in the container 51 in this embodiment is used for measuring the dissolved oxygen concentration in the sample water, and obtained by dissolving a medicine that develops color by reaction with oxygen (for example, indigocarmine) along with a reducing agent in a solvent such as water or an alcohol compound (in particular, a polyalcohol compound such as a glycol compound).

Figure 4:
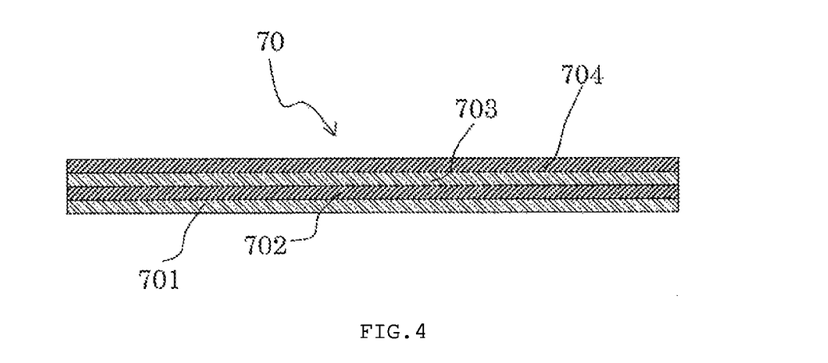
FIG. 4 is a cross-sectional view illustrating one example of a sheet used for the medicine package.
Figure 5:
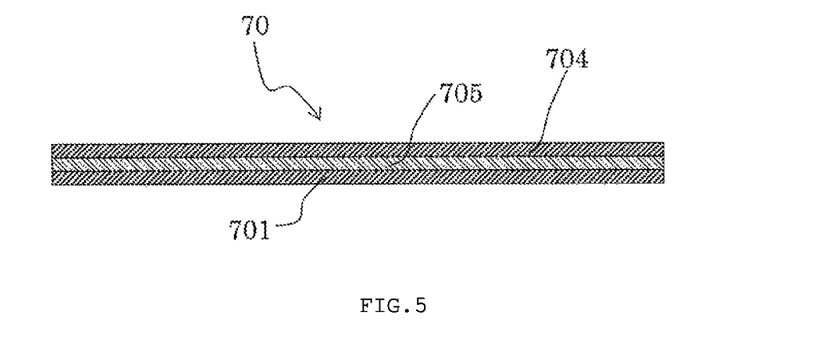
FIG. 5 is a cross-sectional view illustrating another example of the sheet used for the medicine package.

In order to improve preservation stability of a reagent, it is desirable that the sheet 70 used herein has gas barrier properties and light-blocking properties allowing to prevent intrusion of the external air, as well as chemical resistance and heat welding properties within the container 51. Examples of the sheet 70 include a four-layer sheet in which, as shown in FIG. 4, a linear low density polyethylene resin film layer 701, a stretch polyamide resin film layer 702, an aluminum foil layer 703, and a stretch polyethylene terephthalate resin film layer 704 are laminated from an interior to an exterior of the container 51 with an adhesive layer interposed between the layers. The examples of the sheet 70 also include a three-layer sheet, as shown in FIG. 5, the linear low density polyethylene resin film layer 701, an aluminum oxide vapor deposition polyamide resin film layer 705, and the stretch polyethylene terephthalate resin film layer 704 are laminated from the interior to the exterior of the container 51 with an adhesive layer interposed between the layers. In a case in which such a laminated sheet is used, the container 51 can be formed by heat-welding inner surfaces of the several pieces of sheets 70 cut in a desired shape with each other. It should be noted that various adhesives, including a polyurethane-based, an epoxide-based, a polyester-based, a cyanoacrylate-based, a polyacrylic-acid-ester-based, and a polyvinyl acetate adhesives, can be used as the adhesive layer in the laminated sheets.

The tube body 52 is a component made of a resin having chemical resistance and both ends of the tube body are open (for example, a molded product made of a high-density polyethylene resin), and includes a connector unit 52a, on one end, whose diameter is contracted. In addition, a first receiving section 52b that engages with the tube body stopping piece 45a of the cartridge case 41 is provided substantially in a central portion of an outer circumference of the tube body 52 in a length direction. The tube body 52 is disposed so as to connect the interior and the exterior of the container 51 at a lower end of the container 51 in a central potion, and a portion of the tube body 52 from the first receiving section 52b to the connector unit 52a protrudes from the container 51.

Here, the inner surface of the sheet 70 is adhered to an outer circumferential surface of an end portion of the tube body 52 disposed within the container 51 in an air tight manner. Further, an inclined section 72 is provided for an adhered section between the sheets 70 such that a lower part of the interior, i.e., an internal space, of the container 51 forms a funnel shape along with the tube body 52 as a stem.

The tube 53 is made of an elastic material, and coupled with the tube body 52 by inserting the connector unit 52a of the tube body 52 into one end of the tube.

Examples of the elastic material that forms the tube 53 include a binary fluorine rubber such as a copolymer of vinylidene fluoride and hexafluoropropylene. As the binary fluorine rubber is superior in gas barrier properties (in particular, oxygen barrier properties) and chemical resistance, the binary fluorine rubber is particularly suitable when the reagent contained in the container 51 is a redox reagent for measuring the dissolved oxygen concentration in the sample water. In general, the tube 53 can be formed by press molding.

Figure 6:
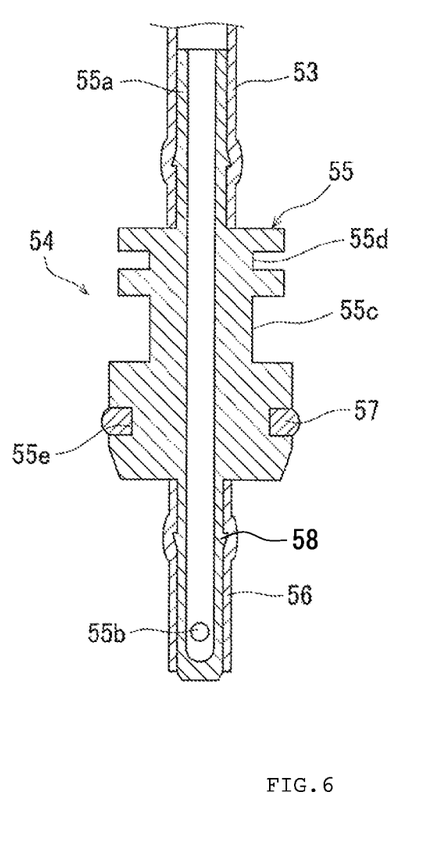
FIG. 6 is a vertical cross-sectional view illustrating a nozzle provided for the medicine package.

The nozzle 54 is configured to discharge the reagent contained in the container 51, and connected to a tip end of the tube 53. As shown in FIG. 6, the nozzle 54 includes a nozzle main body 55 in a tubular shape whose base end is open and tip end is closed, and a valve rubber 56 (i.e. a second tube) attached around an outer circumferential surface of the nozzle main body 55 on the tip end side. The nozzle main body 55 is a component made of a resin having chemical resistance (for example, a molded product made of a high-density polyethylene resin), and an inner diameter of the nozzle main body 55 is set to be even in the length direction. On the base end side of the nozzle main body 55, a connector unit 55a is provided, and the connector unit 55a is inserted into the tip end of the tube 53. Further, in either side surface of the nozzle main body 55 on the tip end side, there is provided a discharge hole 55b penetrating through the side surface in a direction perpendicular to a center axis of the nozzle main body 55. Specifically, the nozzle main body 55 includes two discharge holes 55b that communicate with an interior of the nozzle main body 55. As shown in FIG. 6, the nozzle main body 55 has a barb 58 provided on an outer circumferential surface close to the tip end. Further, a thick stepped section 55c is provided in a substantial central portion of the nozzle main body 55 in the length direction around the outer circumference. A second receiving section 55d that engages with the nozzle stopping piece 45e of the cartridge case 41 is provided around the outer circumference of the stepped section 55c on the base end side. Further, a groove 55e is provided around the outer circumference of the stepped section 55c on the tip end side, and a seal ring 57 (for example, a D ring made of a fluorine rubber) is attached to the groove 55e. The valve rubber 56 is a tube made of an elastic material having chemical resistance (for example, a polyolefin rubber (i.e. a polyolefin elastomer)), attached around the outer circumferential surface of the nozzle main body 55 on the tip end side and covers the barb 58 so as to be retained to the nozzle main body 55 and to close the two discharge holes 55b.

The medicine package 50 described above is configured such that the first receiving section 52b of the tube body 52 is engaged with the tube body stopping piece 45a of the cartridge case 41, and the container 51 is disposed upright within the container housing 44. Further, the tube 53 extends downward within the roller in-out unit 45, and the second receiving section 55d of the nozzle main body 55 is engaged with the nozzle stopping piece 45e of the cartridge case 41. As a result, the fluid reagent contained in the container 51 fills the tube 53 through the tube body 52, and an outflow of the fluid reagent through the discharge hole 55b of the nozzle main body 55 is prevented by the valve rubber 56. It should be noted that when the reagent cartridge 40 is attached, the nozzle 54 is disposed such that a tip end section thereof protrudes into the measurement cell 10, and attached to an inner surface of the measurement cell 10 in an air tight manner by the seal ring 57.

The discharge mechanism 60 is configured to discharge the reagent contained in the container 51 of the medicine package 50, and includes a rotary driving shaft 61 connected to a motor that is not illustrated, a driving arm 62, and a pressing roller 63 as major components. The rotary driving shaft 61 is provided outside the slit 45b and rotatable in a counterclockwise direction in FIG. 2. One end of the driving arm 62 is coupled to the rotary driving shaft 61, and the pressing roller 63 is rotatably attached to the other end. The driving arm 62 is rotatable in the counterclockwise direction by rotation of the rotary driving shaft 61, as shown by a chain-double dashed line in FIG. 2, and configured to allow the pressing roller 63 to come into and out from the roller in-out unit 45 through the slit 45b by this rotation of the driving arm 62.

The water quality measuring device 1 described above is provided with a control unit 90 (see FIG. 1), and measures the dissolved oxygen concentration in the sample water by the control unit 90 controlling operations of the respective components as described in the following description.

Next, an operation of water examination of the sample water by the water quality measuring device 1 will be described.

First, the electromagnetic valve 15 of the water quality measuring device 1 is set to an open state. With this, the sample water flows into the measurement cell 10 from the flow channel 2 through the inlet channel 12. At this time, foreign substances contained in the sample water are removed through the filter 13. Further, an amount of the sample water that flows into the measurement cell 10 is controlled by the constant flow valve 14. The sample water continuously flowing into the measurement cell 10 fills the measurement cell 10, and is continuously discharged through the outlet channel 16. At this time, when the electromagnetic induction coil of the stator 17b is energized, a magnetic field generated by the energization is received by the magnet of the agitator 17a, and whereby the agitator 17a within the measurement cell 10 rotates. Accordingly, the sample water that has flowed into the measurement cell 10 is agitated, and the measurement cell 10 is pre-washed by the sample water.

After the pre-washing as described above, when the energization of the electromagnetic induction coil of the stator 17b is suspended and the electromagnetic valve 15 is closed, the inflow of the sample water into the measurement cell 10 is prevented, and the sample water is pooled in the measurement cell 10 up to a level of the outlet channel 16. As a result, a tip end portion of the nozzle 54 is disposed within the pooled sample water. The measuring unit 20 is operated in this state, and light is emitted from the light emitter 21a to the light receiver 21b. Then, intensity of the transmitted light of the light emitted from the light emitter 21a through the sample water is measured.

Next, the energization of the electromagnetic induction coil of the stator 17b is resumed to resume the rotation of the agitator 17a, and the motor of the discharge mechanism 60 is driven at the same time while maintaining this state to rotate the rotary driving shaft 61. As a result, the driving arm 62 rotates in the counterclockwise direction in FIG. 2, and this causes the pressing roller 63 to rub the tube 53 down while pressing the tube 53 against the pressing surface 45c. Then, the reagent that flows from the container 51 into the tube 53 through the tube body 52 is pumped to the nozzle 54, and overflows from the discharge hole 55b of the nozzle main body 55. With this, a gap is provided between the nozzle main body 55 and the valve rubber 56, and through this gap, a certain amount of reagent is discharged into the sample water within the measurement cell 10. Therefore, by repeating the rotational movement of the driving arm 62, the certain amount of reagent is intermittently injected into the sample water every time the driving arm 62 rotates.

In this case, as the container 51 is configured by the soft sheets 70 and includes the gusset 71 on each side, the container 51 shrinks such that the gussets 71 are closed as the reagent is discharged through the nozzle 54. Thus, the container 51 allows the reagent to be discharged through the nozzle 54 without causing external air to enter, and is able to stably maintain the contained reagent without causing denaturation due to an influence of the external air. Further, as the internal space of the container 51 is formed in a funnel shape as described above, the contained reagent can be smoothly directed toward the tube body 52, and whereby the reagent can smoothly flow into tube body 52. Therefore, it is possible to use up the reagent contained in the container 51 to the last drop.

The reagent thus injected into the measurement cell 10 is dissolved into the sample water that is agitated by the rotation of the agitator 17a, and reacts with dissolved oxygen contained in the sample water to change the color of the sample water.

In the step of reagent injection as described above, the control unit 90 maintains the rotation of the agitator 17a, and causes the measuring unit 20 to continuously measure intensity of transmitted light (I) of the sample water that changes its color by the gradually injected reagent. At this time, the control unit 90 determines an amount of change in the intensity of transmitted light associated with an increase of the amount of the reagent injected into the sample water. The amount of change in the intensity of transmitted light determined here is usually taken as a difference between the intensity of transmitted light before and after the certain amount of reagent is injected ($\Delta I$). In general, the intensity of transmitted light of the sample water gradually decreases according to the number of times that the reagent is injected (i.e., the number of times of the rotational movement of the driving arm 62) increases. In this case, if all the dissolved oxygen in the sample water has reacted with the reagent that has been injected in the Xth time and before, it is difficult to further change the color of the sample water by injecting more reagent in the injecting operation after the Xth time, and the intensity of transmitted light of the sample water is less likely to change. Specifically, a difference between intensity of transmitted light $I^1$ after the Xth time of the reagent injection and intensity of transmitted light $I^2$ after the (X+1)th time of the reagent injection ($I^1-I^2$, i.e., ΔI described above) is very small. Therefore, once ΔI reaches a predetermined amount or smaller, the reagent injected into the sample water thereafter remains as it is in the sample water without affecting the reaction with the dissolved oxygen in the sample water.

Accordingly, the control unit 90 stops the rotation of the driving arm 62 when it is determined that ΔI has reached the predetermined amount or smaller. This stops additional injection of the reagent to the sample water. Subsequently, the control unit 90 obtains a ratio between intensity of transmitted light ($I^B$) of the sample water at this time and intensity of transmitted light ($I^A$) of the sample water before injecting the reagent (ratio of intensity of transmitted light $I^B/I^A$). Then, based on previously prepared data for standard curves of the ratio of intensity of transmitted light and the dissolved oxygen concentration, the control unit 90 calculates the dissolved oxygen concentration in the sample water.

After measuring the dissolved oxygen concentration in the sample water in this manner, the agitator 17a is again rotated and the electromagnetic valve 15 is opened, and the reagent-containing sample water pooled in the measurement cell 10 is pushed out by the sample water that newly flows through the inlet channel 12, and is discharged through the outlet channel 16. In this manner, the cleaning of the measurement cell 10 is completed.

It should be noted that in the water examination of the sample water as described above, when the reagent filled within the medicine package 50 runs out, although it is possible to replace only the medicine package 50 by removing the reagent cartridge 40 and dividing the cartridge case 41 into the front case 42 and the back case 43, it is usually preferable to replace the removed reagent cartridge 40 as a whole with a new one.

The above embodiment describes the case in which the reagent for measuring the dissolved oxygen concentration in the sample water is contained in the container 51 of the medicine package 50 is described. However, the reagent (medicine) can be a different reagent for measuring a different water quality index of the sample water such as residual chlorine concentration, hardness, silica concentration, M alkalinity, or pH, for example. In this case, when measuring residual chlorine concentration, similarly to the case of the measurement of dissolved oxygen concentration, it is necessary to use a redox reagent (medicine) that is susceptible to denaturation due to the external air. However, for the other water quality indices, a reagent that is insusceptible to an influence of the external air, such as a chelating agent or a complexing agent, can be used. Therefore, for the medicine package 50 for measuring a different water quality index, it is possible to use a polyolefin rubber (i.e. a polyolefin elastomer) such as "PharMed", which is a trademark of Saint-Gobain K.K. as an elastic material formed into the tube 53. In this case, the tube 53 can be formed by extrusion molding.

What is claimed is:

1. A The water quality measuring device comprising:
a measurement cell configured to pool sample water;
a sample water supply unit configured to supply the measurement cell with sample water;
a reagent supply unit configured to supply the measurement cell with a reagent to react with a water quality index substance;
an agitating unit provided at a bottom of the measurement cell;
a measuring unit configured to measure intensity of transmitted light of light having a required wavelength through sample water; and
a control unit configured to control operations of the sample water supply unit, the reagent supply unit, the agitating unit, and the measuring unit; wherein
the sample water supply unit includes an inlet channel configured to supply the measurement cell with sample water and an outlet channel configured to discharge sample water from the measurement cell,
the inlet channel is connected to a flow channel configured to supply sample water, and includes a filter and an electromagnetic valve,
the control unit opens the electromagnetic valve for supplying sample water to allow sample water, from which foreign substances are removed by the filter, to flow into the measurement cell,
the inlet channel further includes a constant flow valve,
the control unit opens the electromagnetic valve for supplying sample water to allow sample water, from which foreign substances are removed by the filter and of which flow rate is controlled by the constant flow valve, to flow into the measurement cell,
the measurement cell has a pair of light transmission windows facing each other and provided in side walls,
the measuring unit includes a light-emitting diode and a phototransistor facing each other with the light transmission windows sandwiched therebetween,
in a state where the measurement cell pools sample water from which foreign substances are removed by the filter, the control unit operates the measuring unit to measure intensity of transmitted light through the sample water,
the agitating unit includes an agitator rotatably provided on the bottom of the measurement cell and a stator provided outside the measurement cell,
the control unit energizes an electromagnetic induction coil of the stator to rotate the agitator while sample water is supplied and the reagent is injected,
the reagent supply unit includes a reagent cartridge removably provided at an opening of the measurement cell,
the reagent cartridge includes a cartridge case and a medicine package housed in the cartridge case,
the medicine package includes a container configured to contain the reagent, a tube body provided at a lower edge of the container and configured to connect an interior and an exterior of the container, a first tube having a first end coupled to the tube body and made of an elastic material, and a nozzle connected to a second end of the first tube and configured to discharge the reagent,
the nozzle includes a nozzle main body having a closed tip end and a second tube made of an elastic material,
the nozzle main body has a discharge hole penetrating a side surface close to the tip end and a barb provided on an outer circumferential surface close to the tip end, and
the second tube is attached to the tip end of the nozzle main body and covers the barb, to be retained to the nozzle main body and close the discharge hole.

2. The water quality measuring device according to claim 1, wherein
the elastic material for the first tube is binary fluorine rubber or polyolefin elastomer, and
the elastic material for the second tube is polyolefin elastomer.

3. The water quality measuring device according to claim 2, wherein
the nozzle main body includes a stepped section provided substantially in a center of an outer circumference in a length direction, a groove provided around an outer circumference of the stepped section close to a tip end, and a seal ring attached to the groove, and
when the reagent cartridge is attached, the nozzle is disposed such that a tip end of the nozzle protrudes into the measurement cell and airtightly attached to an inner circumferential surface of the measurement cell by the seal ring.

4. The water quality measuring device according to claim 3, wherein
the cartridge case includes a container housing and a tubular portion extended from a bottom surface of the container housing,
the tubular portion includes a slit provided vertically, a curved surface recessed arcuately and provided substantially in a vertical center of a surface facing the slit, a tube body stopping piece provided at a base end, and a nozzle stopping piece provided at a tip end,
the tube body includes a first receiving section provided at a portion protruding from the container,
the nozzle main body includes a second receiving section provided at a base end,
the container is disposed in the container housing with the first receiving section being engaged with the tube body stopping piece, and
the first tube is disposed in the tubular portion with the second receiving section being engaged with the nozzle stopping piece.

5. The water quality measuring device according to claim 4, wherein
the reagent supply unit further includes a discharge mechanism configured to discharge the reagent from the reagent cartridge to the measurement cell,
the discharge mechanism includes a rotary driving shaft provided outside the slit and connected to a motor, a driving arm having a first end coupled to the rotary driving shaft, and a pressing roller rotatably attached to a second end of the driving arm, the reagent is discharged into sample water from the discharge hole through a gap provided between the nozzle main body and the second tube when the pressing roller entering and exiting the slit presses the first tube toward the curved surface, and
the control unit drives the motor of the discharge mechanism for injecting the reagent, to intermittently inject a certain amount of the reagent into sample water every time the driving arm rotates.

6. The water quality measuring device according to claim 5, wherein
the container is entirely configured by soft sheets and provided as a bag having a gusset on either side, the interior of the container through lamination of interior surfaces of the soft sheets formed in a funnel shape with the tube body as a stem.

7. The water quality measuring device according to claim 6, wherein
each of the soft sheets is configured as a laminated sheet including a linear low density polyethylene resin film layer, a stretch polyamide resin film layer, an aluminum foil layer, and a stretch polyethylene terephthalate resin film layer, laminated from inside to outside of the container.

8. The water quality measuring device according to claim 6, wherein
each of the soft sheets is configured as a laminated sheet including a linear low density polyethylene resin film layer, an aluminum oxide vapor deposition polyamide resin film layer, and a stretch polyethylene terephthalate resin film layer, laminated from inside to outside of the container.

* * * * *